R. KORDES
ROSE PLANT
Filed Sept. 18, 1974
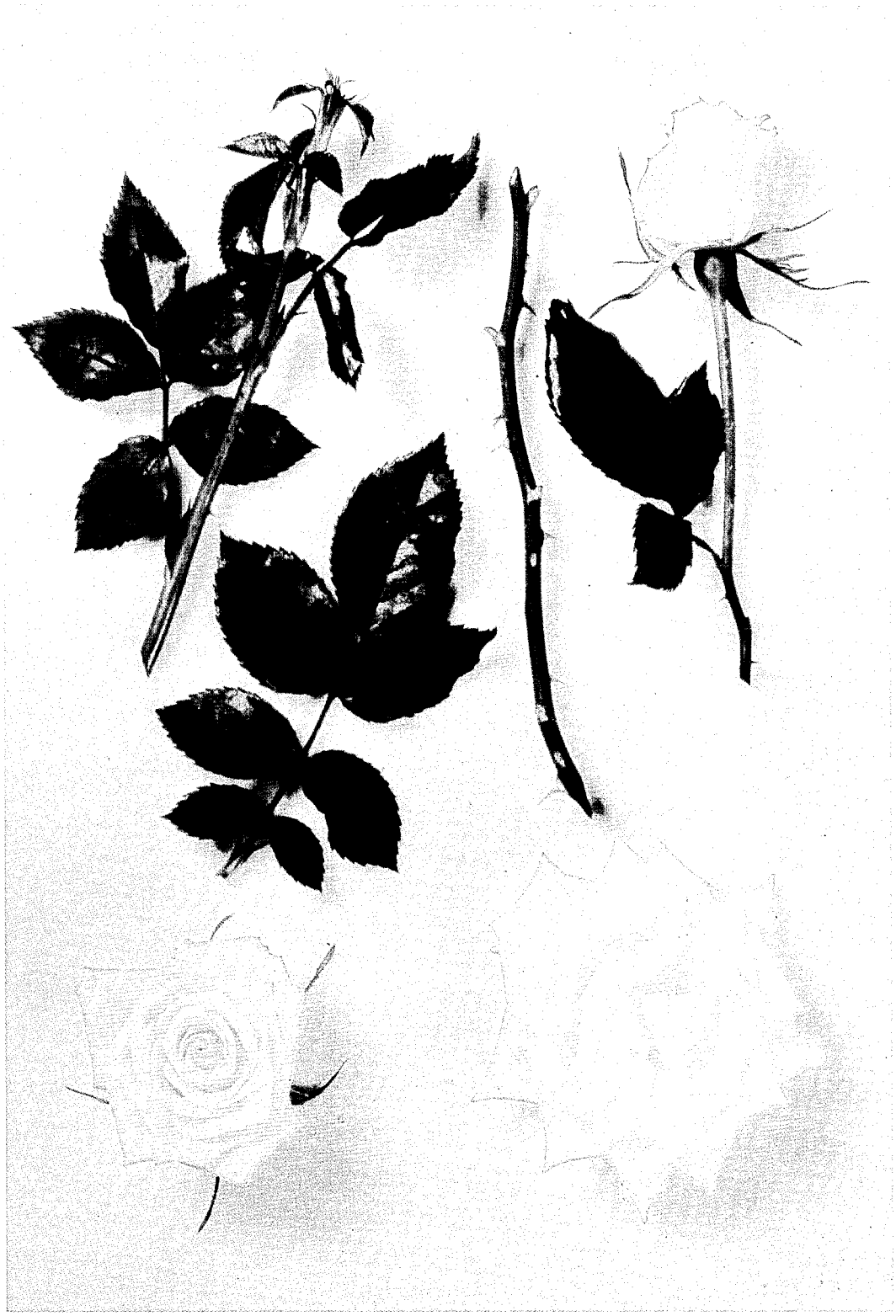

United States Patent

Plant Pat. 3,789
Patented Sept. 23, 1975

3,789
ROSE PLANT

Reimer Kordes, Sparrieshoop, near Elmshorn, Holstein, Germany, assignor to Jackson and Perkins Company, Medford, Oreg.

Filed Sept. 18, 1974, Ser. No. 506,996
Int. Cl. A01h *5/00*
U.S. Cl. Plt.—25 1 Claim

The present invention relates to a new and distinct cultivar of rose plant of the floribunda class which was originated by me by crossing the cultivar Konigen der Rosen with pollen from the cultivar Zorina, U.S. Plant Pat. No. 2,321.

The primary objective of this breeding was to produce a new cultivar of the floribunda class bearing flowers similar to Zorina but of better substance, longer vase life, and better foliage.

This objective was fully achieved along with other desirable improvements as evidenced by the following unique combination of characteristics which are outstanding in this new cultivar and which distinguish it from its parents as well as from all other cultivars of which I am aware:

1. A bushy, well branched, large clustered plant when grown outside, relatively shorter than the cultivar, Prominent, U.S. Plant Pat. No. 3,380.
2. Bud and flower color similar to that of Prominent but generally lighter, such as Fire Red (15) compared to Capsicum Red (715) of Prominent, in the half open stage.
3. Glossy foliage.
4. Leaflets are generally narrower and more pointed than leaflets of the cultivar Prominent.
5. Little or no fragrance.
6. Very strong petal substance.

Asexual reproduction of this new cultivar by budding as performed at Sparrieshoop, West Germany, and Irvine, Calif., shows that the aforementioned characteristics come true to form and are established and transmitted through succeeding propagations.

The accompanying illustration shows typical specimens of the vegetative growth and flowers of this new cultivar in different stages of development and as depicted in color as nearly true as it is seasonably possible to make the same in a color illustration of this character.

The following is a detailed description of my new rose variety with color terminology in accordance with Wilson's Horticultural Color Chart, except where ordinary dictionary significance is indicated.

Parentage: Seedling.
- *Seed parent.*—Color Wonder (Konigen der Rosen).
- *Pollen parent.*—Zorina, U.S. Plant Pat. No. 2,321.

Classification:
- *Botanic.*—Rosa hybrid.
- *Commercial.*—Floribunda.

FLOWER

Observations were made at Irvine, Calif., in early June.

Blooming habit: Recurrent-continuous.

Bud:
- *Size.*—⅞ inch to 1 inch when petals start to unfurl.
- *Form.*—Long, blunt top.
- *Color.*—When sepals first divide near Capsicum Red (715/1) with large area at base near Chrome Yellow (605/2) suffusing into most of petal area. When half blown; upper side of petals near Fire Red (15) with sharply defined area near Chrome Yellow (605) at petal base; lower side of petals near Fire Fed (15/1) suffused slightly with Chrome Yellow (605/2) and large area near base of Chrome Yellow (605/2).

- *Sepals.*—Color: Outer surface Scheeles Green (860). Inner surface Scheeles Green (860/3) with moderate covering of white tomentum. Three appendaged sepals heavily appendaged. Two unappendaged sepals hairy edged.
- *Receptacle.*—Color: Sheeles Green (860). Shape: Funnel. Size: Long. Surface: Smooth.
- *Peduncle.*—Length: Medium. Surface: Prickly. Color: Scheeles Green (860). Strength: Stiff, erect.
- *Opening.*—Nearly spiral with petals moderately pointed.

Bloom:
- *Size.*—Medium. Average open size 2½ inches to 3 inches.
- *Borne.*—Singly and in flat clusters.
- *Stems.*—Medium.
- *Form.*—When first open—high center. Permanence—retains its form to the end.
- *Petalage.*—Number of petals under normal conditions—30
- *Color.*—Center of flower: Upper side of petals near Fire Red (15), Chrome Yellow (605) at base of petal. Reverse side of petals near Fire Red (15/1) suffused slightly with Chrome Yellow (605/2) and large area near base of Chrome Yellow (605/2). General tonality from a distance Fire Red (15).
- *Discoloration.*—At end of first day—No change. Third day—slightly lighter than freshly opened flower.
- *Fragrance.*—Slight.
- *Petals.*—Thick.
- *Shape.*—Broadly oval.
- *Form.*—Edges slightly quilled.
- *Arrangement.*—Imbricated.
- *Petaloids in center.*—Few.
- *Persistence.*—Drop off cleanly.
- *Lastingness.*—On the plant—very long. As cut flower—very long.

Reproductive parts:
- *Anthers.*—Large. Color—yellow. Arrangement—regular around styles.
- *Filaments.*—Color—yellow.
- *Pollen.*—Gold yellow.
- *Styles.*—Color—near white.
- *Stigmas.*—Color—light yellow.

PLANT

Form: Bush.

Growth: Very vigorous, upright, branching.

Foliage: Number of leaflets on normal mid-stem leaves, 5–7.
- *Size.*—Medium.
- *Quantity.*—Normal.
- *Color.*—New foliage: Garnet Brown (00918/3) suffused with a green between Emerald Green (758) and Spinach Green (0960). Old foliage: Between Emerald Green (758) and Spinach Green (0960).

Leaflets:
- *Shape*: Oval pointed.
- *Texture.*—Upper side—glossy.
- *Edge.*—Serrated.
- *Serration.*—Single.
- *Petiole.*—Rachis — Color — Reddish. Underside—prickles.
- *Stipules.*—Long, bearded.
- *Disease resistance.*—Resistant to mildew under normal growing conditions at Irvine, Calif.

Wood:
- *New wood.*—Color—Light green. Bark—Smooth.
- *Old wood.*—Color—Green. Bark—Smooth.

Prickles:

*Quantity.*—On main stalks from base—ordinary. On laterals from stalk—ordinary.

*Form.*—Narrow base. Long, hooked slightly downwardly.

*Color when young.*—Brown.

*Position.*—Irregular.

Small prickles:

*Quantity.*—On main stalks—few. On laterals—few

*Color.*—Brown.

I claim:

1. A new and distinct cultivar of rose plant of the floribunda class, substantially as herein shown and described, characterized particularly as to novelty by the unique combination of buds and flowers being of similar hue to the cultivar Prominent, U.S. Plant Pat. No. 3,380, but of a lighter shade, a compact, well branched plant, glossy leaves, the leaflets being proportionately more narrow than those of Prominent, a high degree of resistance to rose powdery mildew, and very little fragrance.

No references cited.

ROBERT E. BAGWILL, Primary Examiner